United States Patent [19]

Schirmer et al.

[11] Patent Number: 4,907,872
[45] Date of Patent: Mar. 13, 1990

[54] CONTACT LENS FOR ENABLING TREATMENT OF THE EYE BY LASER

[75] Inventors: K. E. Schirmer, Montreal, Canada; Werner Reis, Munich, Fed. Rep. of Germany

[73] Assignee: G. Rodenstock Instrumente GmbH, Munich, Fed. Rep. of Germany

[21] Appl. No.: 201,759

[22] Filed: Jun. 3, 1988

[30] Foreign Application Priority Data

Jun. 3, 1987 [DE] Fed. Rep. of Germany ....... 3718599

[51] Int. Cl.$^4$ ............................ G02C 7/04; A61B 3/00
[52] U.S. Cl. .................................. 351/160 R; 351/219
[58] Field of Search ............... 351/160 R, 160 H, 161, 351/162, 219

[56] References Cited

U.S. PATENT DOCUMENTS 4,506,962 3/1985 Roussel ........................... 351/219 X
4,598,984 7/1986 Rol ..................................... 351/219
4,664,490 5/1987 Rol ..................................... 351/219

Primary Examiner—Scott J. Sugarman
Attorney, Agent, or Firm—Antonelli, Terry & Wands

[57] ABSTRACT

A contact lens is disclosed, especially for the treatment of the frontal eye sections with a laser, the surface on the eye side of which has a radius adapted to the radius of curvature of the cornea, this contact lens exhibiting a reflective surface for enlarging the field of vision.

The contact lens has the following features:

the reflective surface is a planar area and is arranged in the part of the contact lens wherein the axial distance between the surface on the eye side and the frontal surface is at a maximum, the surfaces on the eye side and on the frontal side form an aplanatic system, the two surfaces almost penetrate each other on the side opposite to the reflective surface.

6 Claims, 1 Drawing Sheet

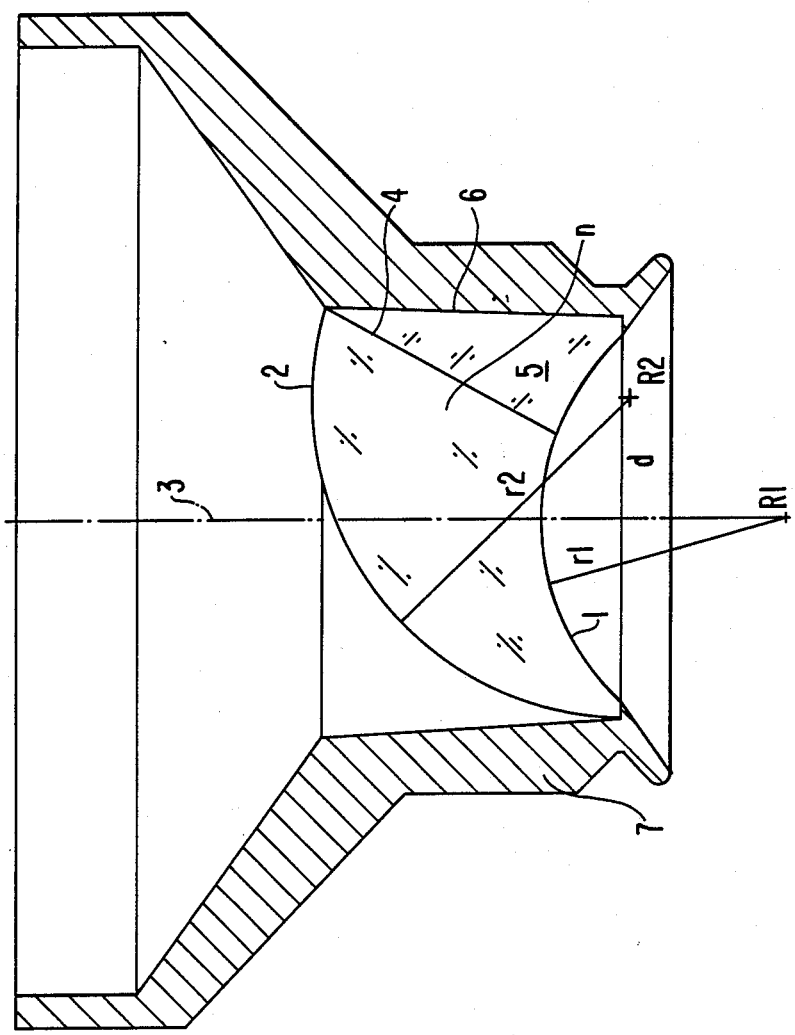

CONTACT LENS FOR ENABLING TREATMENT OF THE EYE BY LASER

FIELD OF THE INVENTION

The invention relates to a contact lens, especially for treatment of frontal eye sections wth a laser.

Such contact lenses are utilized, especially in the treatment of glaucoma with a neodymium YAG laser.

DESCRIPTION OF THE PRIOR ART

A contact lens of this type has been known, for example, from U.S. Pat. No. 4,598,984. However, this conventional contact lens has a number of disadvantages:

On the one hand, the reflective surface and thus the "field of vision" is comparatively small. On the other hand, the image errors are not particularly well corrected in this known contact lens.

SUMMARY OF THE INVENTION

The present invention has an object of further developing a contact lens usable especially for the treatment of the frontal eye sections with a laser in such a way that, with satisfactory optical imaging properties, a large visual field angle can be attained.

This object can be obtained surprisingly by furthermore starting with a contact lens of the aforementioned type and further developing this contact lens of the type applicable herein by the combination of the following features:

the reflective surface is a planar area and is arranged in the part of the contact lens wherein the axial distance of the surface on the eye side and the frontal surface is at a maximum, the surfaces on the eye side and on the frontal side form an aplanatic system, the two surfaces almost penetrate each other on the side opposite to the reflective surface.

This arrangement in accordance with the invention makes it possible, on the one hand, to choose the radius of curvature of the frontal surface in such a way that the frontal surface lends a considerable contribution toward the optical effect, an arrangement being obtained by the decentering of the two surfaces, provided by the invention, wherein the "thickest" point, i.e. the site where the axial distance of the two surfaces is at a maximum, in the contact lens, does not lie in the geometric center of the two surfaces. This ensures that with an eccentric mirror arrangement as required for a large visual field angle for the observation beam path and, respectively, the treatment laser beam, the mirror can have comparatively large dimensions. As a consequence, even with a small and lightweight structure as needed precisely in case of contact lenses, a large visual field and, respectively, a large laser angle are possible.

Furthermore, the two surfaces constitute, according to this invention, an aplanatic system. As a result, not only is the numerical aperture increased, but also the aperture error and the coma are corrected and the back focal distance is shortened so that, in spite of the large visual field angle, a substantially improved imaging is obtained for observation and laser treatment.

On account of the third feature of the characterizing portion, a large "off-axis" thickness is obtained on one half of the lens even with an otherwise small and lightweight contact lens.

According to another, the reflective surface inclined with respect to the ocular axis penetrates at its outer rim the peripheral rim of the second surface. By this construction, the thickness of the lens is particularly well utilized by the arrangement of the mirror. As a consequence of these measures, a reflector located far on the outside is obtained having large dimensions so that the visual field angle and the field of vision are substantially larger than in conventional contact lenses.

BRIEF DESCRIPTION OF THE DRAWING

The invention will be described in greater detail below by means of an example with reference to the drawing, the single figure of which shows a longitudinal section through the embodiment.

DESCRIPTION OF THE PREFERRED EMBODIMENT

The contact lens according to the invention comprises a surface 1 on the side of the eye and a second (frontal) surface 2 through which there take place the observation and, respectively, the beaming in of the treatment light.

The radius of curvature r1 of surface 1 is chosen in correspondence with the corneal radius of the eye to be examined and/or treated (not shown), so that the contact lens can be placed conventionally on the eye with (extensively) flat contact. The center of curvature R1 of surface 1 lies on an axis 3 coinciding with the ocular axis.

In contrast thereto, the center of curvature R2 of surface 2 is not located on axis 3 but rather is laterally offset by an amount d so that the two surfaces are not centered.

On account of this feature, the axial thickness of the contact lens becomes larger in the lateral zone wherein a reflective surface 4 is arranged than in case of a centered lens so that the usable reflecting area is substantially enlarged. As a consequence, the visual angle and the size of the field of vision are markedly increased as compared with the state of the art.

The reflective surface 4 can be produced in a simple way by cementing a mirror-equipped wedge 5 in place.

The illustrated embodiment exhibits the data set forth below, without limiting the generality:

Radius r1 of the surface on the eye side: 8.00 mm

Radius r2 of the second surface: 10.52 mm

Inclination of the reflective surface with respect to the ocular axis: 30°

Displacement d of the centers of rotation of the two surfaces in the direction perpendicularly to the ocular axis: 4.0 mm Distance of the centers of rotation of the two surfaces in the direction of the ocular axis: $\approx 2.4$ mm Diameter of contact lens: 13.0 mm Index of refraction: n=1.518.

In the illustrated embodiment, the two surfaces 1 and 2 almost intersect on the side opposite to the mirror 4. This likewise contributes toward a further increase in the dimensions of the mirror without incurring an excessive increase in the "axial" thickness of the lens and in the weight thereof.

Furthermore, the two surfaces 1 and 2 form an aplanatic system so that good imaging properties result.

The structure of the contact lens according to this invention with two decentered surfaces moreover has the additional advantage that the contact lens has a relatively large planar surface 6 over a portion of the peripheral rim, usable for example for cementing the lens in this region to a mount 7 so that a secure hold is obtained with low manufacturing expenditure.

The invention has been described in the foregoing with reference to embodiments. Of course, a great variety of modifications are possible within the general scope of the idea of this invention: Thus, the numerical data can, of course, be adapted to certain requirements and/or to the wavelength of the treatment light.

We claim:

1. A contact lens for enabling treatment of frontal eye sections with a laser, the contact lens having a surface provided on the eye side with a radius adapted to the radius curvature of the cornea, a frontal surface of the contact lens being decentered with respect to the surface on the eye side, and a reflective surface inclined with respect to the ocular axis for enlarging the field of vision, the reflective surface being a planar area arranged in a part of the contact lens where the axial distance of the surface on the eye side and the frontal surface is at a maximum, the surface on the eye side and the frontal surface forming an aplanatic system, and the surface on the eye side and the frontal surface being disposed so as to almost intersect each other on a part of the contact lens opposite to the reflective surface.

2. A contact lens according to claim 1, characterized in that the reflective surface which is inclined with respect to the ocular axis intersects at an outer rim thereof the peripheral rim of the frontal surface.

3. A contact lens according to the claim 1, characterized in that the frontal surface has a radius of curvature different than the radius of curvature of the surface on the eye side.

4. A contact lens according to claim 1 or 2, characterized in that the lens is flatly glued to a mount at least over a portion of the periphery.

5. A contact lens according to claim 1 or 2, characterized by the following data:

radius of the surface on the eye side: 8.00 mm radius of the second surface: 10.52 mm inclination of the reflective surface with respect to the ocular axis: 30° displacement of the centers of rotation of the two surfaces in the direction perpendicularly to the ocular axis: 4.0 mm distance of the centers of rotation of the two surfaces in the direction of the ocular axis: $\approx 2.4$ mm diameter of contact lens: 13.0 mm index of refraction n=1.518.

6. A contact lens according to claim 5, characterized in that the lens is flatly glued to a mount at least over a portion of the periphery.

* * * * *